(12) United States Patent
Keith et al.

(10) Patent No.: US 6,732,579 B2
(45) Date of Patent: May 11, 2004

(54) TURBULENT BOUNDARY LAYER THICKNESS ESTIMATION METHOD AND APPARATUS

(75) Inventors: William L. Keith, Ashaway, RI (US); Kimberly M. Cipolla, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/267,099

(22) Filed: Oct. 8, 2002

(65) Prior Publication Data

US 2004/0065146 A1 Apr. 8, 2004

(51) Int. Cl.$^7$ ................................................. G01M 9/00
(52) U.S. Cl. ................................................. 73/147
(58) Field of Search ................................. 73/147

(56) References Cited

U.S. PATENT DOCUMENTS

| | | | | |
|---|---|---|---|---|
| 4,879,899 A | * | 11/1989 | Leehey | 73/147 |
| 4,896,098 A | * | 1/1990 | Haritonidis et al. | 324/663 |
| 5,199,298 A | * | 4/1993 | Ng et al. | 73/54.01 |
| 5,341,677 A | * | 8/1994 | Maris | 73/147 |
| 5,511,428 A | * | 4/1996 | Goldberg et al. | 73/777 |

* cited by examiner

*Primary Examiner*—Edward Lefkowitz
*Assistant Examiner*—Jermaine Jenkins
(74) *Attorney, Agent, or Firm*—James M. Kasischke; Michael F. Oglo; Jean-Paul A. Nasser

(57) ABSTRACT

A method and apparatus are presented for determining turbulent boundary layer thickness. In this method and apparatus, a pair of sensors are mounted to a solid surface interfacing with a fluid at two separate stream wise locations. A voltage output from the pair of sensors is recorded and a real non-dimensional value of a correlation coefficient is computed with measured data from the recorded voltage. A laboratory non-dimensional value of the correlation coefficient is independently determined from laboratory data. The real non-dimensional value is compared with the laboratory non-dimensional value to obtain a boundary layer thickness having a value which minimizes a difference between the values of the real non-dimensional value and the laboratory non-dimensional value.

12 Claims, 2 Drawing Sheets

TURBULENT BOUNDARY LAYER THICKNESS ESTIMATION METHOD AND APPARATUS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

This invention generally relates to a technique for turbulent boundary layer thickness estimating using hot film wall shear stress sensors.

More particularly, the invention relates to a technique for estimating turbulent boundary layer thickness in an underwater environment using hot film shear wall stress sensors and correlation coefficients.

(2) Description of the Prior Art

The art for hot wire anemometry has been widely used since the 1950's as a technique for making measurements of velocity and shear stress in experimental fluid mechanics facilities. Non-intrusive hot film sensors were developed in the late 1960's to measure the wall shear or tangential stress. These sensors take advantage of the relationship between the rate of heat transfer from small thermal elements and the local wall shear stress. The wall shear stress is related to the velocity gradient at the wall by the relation:

$$\tau = \mu \frac{\partial u}{\partial y}\bigg|_{y=0} \qquad (1)$$

Since the metal film used is adhered to a hard backing or substrate, the sensor is remarkably robust and useful for underwater applications. Whereas pressure sensors are typically used in both laboratory and real-world settings, hot film sensors have not been implemented as a diagnostic measurement tool on actual underwater or surface vehicles. This invention proposes to extend the range of applications to cases including at-sea testing and tactical operations. Currently, no non-intrusive measurement techniques exist for quantifying the turbulent boundary layer thickness outside of a laboratory environment.

The following patents, for example, disclose devices for detecting turbulent flow, but do not disclose the use of hot film sensors and correlation functions for measuring a turbulent boundary layer as disclosed in the present invention.

U.S. Pat. No. 4,188,823 to Hood;
U.S. Pat. No. 4,350,757 to Montag et al.;
U.S. Pat. No. 4,774,835 to Holmes et al.;
U.S. Pat. No. 4,993,261 to Lambert;
U.S. Pat. No. 5,272,915 to Gelbach et al.; and
U.S. Pat. No. 5,890,681 to Meng.

Specifically, Hood discloses a system for detecting the laminar to turbulent boundary layer transition on a surface while simultaneously taking pressure measurements. The system uses an accelerometer for producing electrical signals proportional to the noise levels along the surface and a transducer for producing electrical signals proportional to pressure along the surface. The signals generated by the accelerometer and transducer are sent to a data reduction system for interpretation and storage.

The patent to Montag et al. discloses a method for making visible by photochemical means residual moisture distributions in, photographic wet film layers subjected to a gas flow. According to the invention, a film diffusely pre-exposed is immersed in an aqueous swelling agent solution which contains either (a) a reducing agent or (b) an alkali. After being exposed to the air stream, the invisible residual moisture profile is immersed in an alcoholic solution of either (a) an alkali or (b) a reducing agent. The half-tone image produced serves for determining stationary local boundary layer thickness distributions, wall shearing stresses, material transfer coefficients and heat transfer coefficients.

Holmes et al. discloses a method of visualizing laminar to turbulent boundary layer transition, shock location, and laminar separation bubbles around a test surface. A liquid crystal coating is formulated using an unencapsulated liquid crystal operable in a temperature bandwidth compatible with the temperature environment around the test surface. The liquid crystal coating is applied to the test surface, which is preferably pre-treated by painting with a flat black paint to achieve a deep matted coating, after which the surface is subjected to a liquid or gas flow. Color change in the liquid crystal coating is produced in response to differences in relative shear stress within the boundary layer around the test surface.

Lambert discloses a fluid flow meter including a sensor mounted on or in the inner surface of a conduit for measuring fluid flow through the conduit where the sensitivity of the sensor is dependent upon the thickness of the fluid boundary layer extending over the sensor. According to the invention, fluid is drawn out of the conduit through an aperture located a predetermined distance upstream of the sensor to remove the boundary layer developed upstream of the sensor thereby rendering the sensor immune to fluctuations in the thickness of the removed boundary layer. At the same time, a fresh boundary layer of reduced thickness and greater stability is initiated over the sensor so as to improve the sensitivity and repeatability of the sensor.

The patent to Gelbach et al. discloses an airflow sensing system for determining the type of airflow flowing over a flight surface. A hot film sensor is driven by a constant voltage feedback circuit that maintains the voltage across the sensor at a predetermined level. A signal processing circuit receives an output signal of the feedback circuit and determines whether the output signal is indicative of laminar, transitional, or turbulent airflow. The transitional airflow is distinguished form turbulent airflow by a signal having significant energy in a low-frequency pass band from 50–80 Hz. The signal processing circuit drives a three-color LED display to provide a visual indication of the type of airflow being sensed.

Meng discloses a method for controlling microturbulence in a medium flowing near a surface. The method includes the steps of measuring the forces acting near or on the surface and using those measurements to determine the state probabilities for the microturbulent events occurring at the surface. The control method then activates selective cells in an array of cells to apply forces at the surface to counteract the microturbulent events and thus reduce turbulence. Each cell has a pair of electrodes and opposing magnetic poles such that when the control method activates a cell, the interaction of the electric field and the magnetic field at the cell creates a Lorentz force normal to the surface.

It should be understood that the present invention would in fact enhance the functionality of the above patents by providing a unique concept for estimating the thickness of a hydrodynamic turbulent boundary layer on undersea vehicles, surface vessels, towed bodies or in a laboratory setting. It utilizes commercially available hot film sensors to non-intrusively measure the thickness of the turbulent boundary layer on a surface.

SUMMARY OF THE INVENTION

Therefore it is an object of this invention to provide a method for measuring a turbulent boundary layer thickness.

Another object of this invention is to provide a method for measuring a turbulent boundary layer thickness using hot film wall shear stress sensors.

Still another object of this invention is to provide a method for measuring a turbulent boundary layer thickness utilizing sensor measurements and correlation coefficients.

A still further object of the invention is to provide a method for measuring turbulent boundary layer thickness in underwater applications.

In accordance with one aspect of this invention, there is provided a method and apparatus for determining turbulent boundary layer thickness. Specifically, a pair of sensors are mounted to a solid surface interfacing with a fluid at two separate stream wise locations. A voltage output from the pair of sensors is recorded and a real non-dimensional value of a correlation coefficient is computed with measured data from the recorded voltage. A laboratory non-dimensional value of the correlation coefficient is independently determined from laboratory data. The real non-dimensional value is compared with the laboratory non-dimensional value to obtain a boundary layer thickness having a value which minimizes a difference between the values of the real non-dimensional value and the laboratory non- dimensional value.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
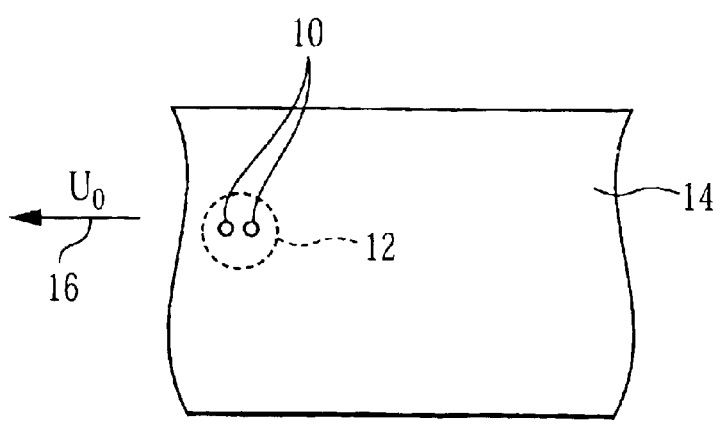
FIG. 1 is a top schematic view of a typical configuration of flush mounted hot film sensors according to the present invention.
Figure 2:
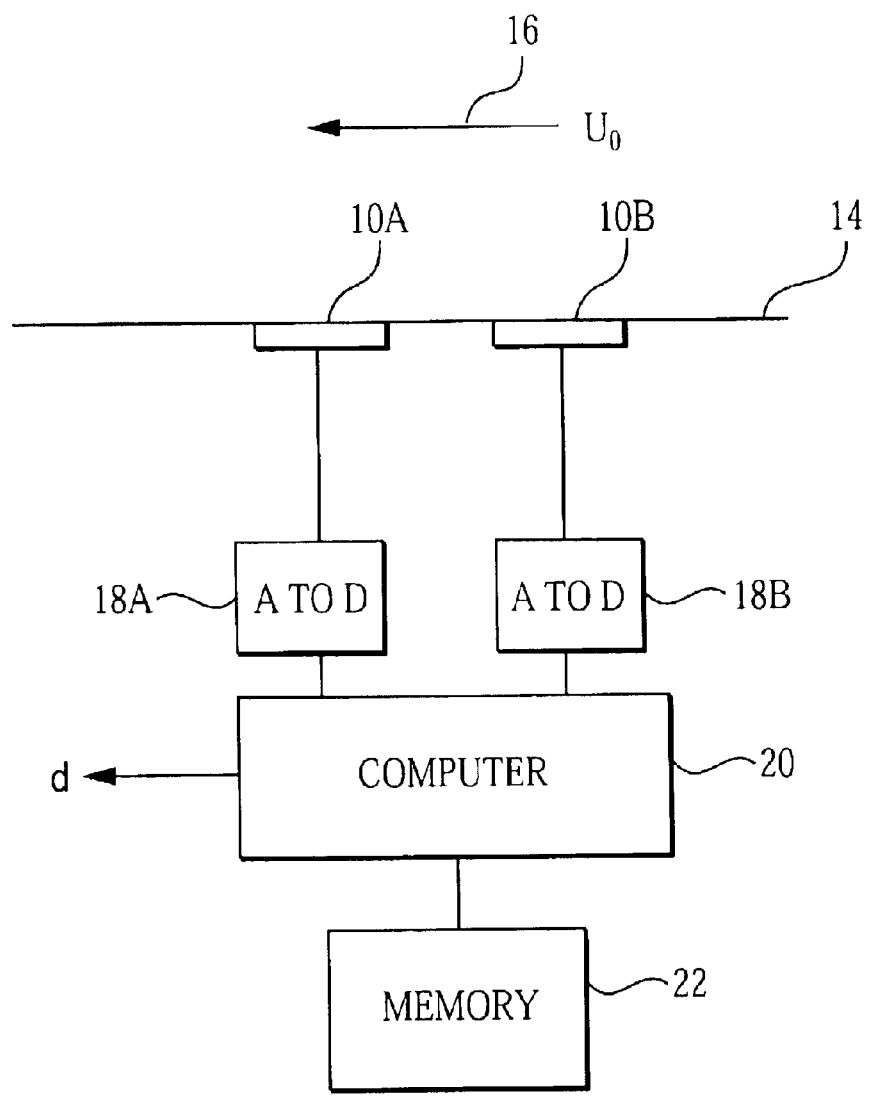
FIG. 2 is a side schematic view of the configuration shown in FIG. 1.

A typical configuration for a relevant application to measure a turbulent boundary layer thickness is shown in FIGS. 1 and 2. In particular, two hot film wall shear stress sensors 10 are housed in a single unit 12 which is mounted flush with a fluid-solid interface 14. A vessel speed is characterized by the label $U_0$ and the vessel direction is shown by arrow 16. Multiple sensor units 12 can be positioned at various locations on a submarine hull or control surfaces (not shown) where boundary layer thickness and/or an indication of separation is of interest.

For example, when positioning a sensor unit 12 at the location of a hull array, a quantitative measure of the boundary layer thickness may be used to optimize the sonar design. Also, monitoring of the sensors 10 for anomalous readings, in conjunction with the acoustic array data, provides a means to determine the source of background noise in the sonar system. Specifically, upstream vortex shedding would be detected by the wall shear stress sensors, while structural vibrations would be detected by the sonar system only. On a control surface, monitoring for the onset of separation can be used to define the operating envelope for quiet, efficient maneuvering. This type of data could then be incorporated into an active control system.

FIG. 2 shows a side view of sensors 10A and 10B and an apparatus for estimating boundary layer thickness $\delta$. Sensor 10A is joined to a first analog to digital converter 18A to provide an analog shear stress measurement. Likewise, sensor 10B is joined to a second analog to digital converter 18B. First and second analog to digital converters 18A and 18B can be a single analog to digital converter having multiple channels. A computer 20 receives digital signals from first and second analog to digital converters, 18A and 18B. The computer 20 is also joined to a memory element 22 having tabulated correlation coefficient values stored therein. The computer 20 can thus receive shear stress measurements and use them to compute a real correlation coefficient. The computer 20 can then compare the real correlation coefficient against tabulated correlation coefficient values stored in memory element 22 in order to provide an estimate of the boundary layer thickness.

Since hot film sensors have a finite area, spatial averaging over the sensor leads to attenuation in the frequency spectra. Unfortunately, the lack of experimental data makes it impossible to quantify this attenuation. Therefore, this invention proposes to use the correlation coefficient (also referred to as the normalized correlation function) as the metric to eliminate the effects of spatial averaging over the frequency range where adequate signal-to-noise exists. The correlation coefficient $R_{\tau_1\tau_2}(\xi_n,T)$ is defined as:

$$R_{\tau_1\tau_2}(\xi_n, T) = \frac{\langle \tau_1(x, t)\tau_2(x+\xi_n, t+T)\rangle}{\sqrt{\langle \tau_1(x, t)^2\rangle} \sqrt{\langle \tau_2(x+\xi_n, t+T)^2\rangle}} \quad (2)$$

where $\tau_1$ and $\tau_2$ are the wall shear stress values at two separate stream wise locations, x is the stream wise coordinate, $\xi_n$ is the discrete sensor spacing, and the < > indicate temporal mean quantities. The estimation of $R_{\tau_1\tau_2}(\xi_N,T)$ is determined digitally in practice, and involves modern analog-to-digital converters and computers. A non-dimensional form of the correlation coefficient, $\hat{R}_{\tau_1\tau_2}(\hat{\xi}_n,\hat{T})$ is obtained by defining $\hat{\xi}_n=\xi_n\times\delta$ and $T=\hat{T}\delta/U_0$, where $\delta$ is the turbulent boundary thickness and $U_0$ is the ship speed or free stream velocity. This leads to a direct relation between the correlation coefficient, $\hat{R}_{\tau_1\tau_2}(\hat{\xi}_n,\hat{T})$ and the turbulent boundary thickness $\delta$.

Knowledge of the turbulent boundary thickness $\delta$ is of particular interest to designers of sonar systems, including hull mounted sonar and towed arrays. Sonar systems must be designed to filter unwanted non-acoustic noise resulting from turbulent boundary layer fluctuations, in order to maximize detection and classification. Design parameters include the structural configuration and the geometry of the sensors themselves. In addition, in-situ measurements of the mean wall shear stress can be used to quantify the skin friction of submarines, unmanned undersea vehicles (UUVs), surface vessels or towed bodies under operating conditions. Reduction of skin friction drag is also of primary interest to the design of racing yachts and high-speed intercept vessels. This is evidenced by the use of riblets on the surface of America's Cup yachts. Detailed measurements of one or more boundary layer parameters on fullscale hulls would provide quantitative information necessary to improve the design. Finally, boundary layer separation resulting from vehicle maneuvers is a concern because it leads to a significant increase in the overall drag of the body. This separation is preceded by an increase in the boundary layer thickness and decrease in the mean wall shear stress, both of which can be detected by the proposed sensors and methodology of the present invention.

An inherent problem with the commercially available technology is the difficulty in calibrating the sensors. Calibration of a single sensor required simultaneous measurements of the mean voltage output from the sensor and the mean velocity profile at the sensor location, from which the mean wall shear stress is calculated. The result of a typical calibration is a polynomial relationship between the wall shear stress, r and the voltage output, v from the sensor, such as, $\tau = aV^3 + bV^2 = cV = d$. The calibration parameter $d\bar{\tau}/d\bar{V}$, is determined from the slope of the calibration curve and used to convert sensor output voltage to wall shear stress. For a complete calibration, the mean velocity and the fluid temperature must be systematically varied, and the measurements repeated. Additional complications include the thermal response of the sensor, spatial averaging due to the sensor size and the non-linearity of the relationship between voltage and mean wall shear stress. For these reasons, the use for flush mounted wall shear stress sensors in laboratory or actual applications has been limited. However, the technique described here uses the normalized correlation coefficient as defined in equation (2). Since the measured root mean square values for each sensor are used to normalize the fluctuation signal in this expression, the calibration parameters cancel.

Thus, the primary purpose of the present technique for turbulent boundary layer thickness estimation using hot film wall shear stress sensors is to obtain an estimation of the turbulent boundary layer thickness in underwater applications. This quantity is often difficult or impossible to measure due to technical limitations of conventional techniques. The intent is to provide an inexpensive method for boundary layer thickness estimation utilizing existing commercially available technology. Conventional laboratory methods such as laser Doppler velocimetry (LDV), hot-wire traverses and pitot tubes are all impractical for actual applications due to physical constraints and the potential for damaging the instruments. Two metrics which could be used are fluctuating wall pressure from piezoelectric sensors and wall shear stress from flush mounted hot film sensors. Both quantities result from velocity fluctuations in the inner and outer regions of the turbulent boundary layer. However, wall shear stress measurements are directly related to the velocity gradient near the wall, while pressure fluctuations measured at the wall are due to both incompressible velocity fluctuations (non-acoustic) in the boundary layer and structural vibrations and acoustic waves in the water. Consequently, any statistical parameter from wall pressure measurements will contain contributions from acoustic and structural sources, which cannot be distinguished from turbulent velocity fluctuation contributions for a given sensor. While an array of wall pressure sensors could be used to distinguish these sources, the present invention instead develops a low-cost system containing a minimum number of sensors and related signal processing. Therefore, the proposed technique uses the wall shear stress as the metric of interest.

The principal of operation is as follows. The voltage from a pair of sensors is recorded and $R_{\tau_1\tau_2}(\xi_n,T)$ is computed from equation (2). The boundary layer thickness is treated as an unknown parameter and used to obtain a non-dimensional value for $R_{\tau_1\tau_2}(\xi_n,T)$. To determine its value, the value of $\hat{R}_{\tau_{12}}(\hat{\xi}_n,\hat{T})$ calculated from the measured data is compared to tabulated values of $\hat{R}_{\tau_1\tau_2}(\hat{\xi}_n,\hat{T})$ obtained in the laboratory. The boundary layer thickness is determined as the value that minimizes the differences between these values. While the sensor is highly sensitive to the temperature of the working fluid, this effect is eliminated by considering a normalized quantity. Measurements of the cross spectral characteristics of wall shear stress were first reported in 1997 and provided quantitative information regarding the convection of shear stress producing structures in the boundary layer.

The advantages of the present invention are numerous. Since the sensors are extremely small and compact, the system can be mounted in experimental facilities or on control surfaces where hot wire probes or pitot tubes are too large and intrusive. Further, the invention utilizes a minimum number of commercially available, inexpensive sensors, commercially available anemometry and minimal processing using PC-based algorithms. The invention has been designed to be compatible with existing laboratory and non-laboratory systems and therefore can be easily installed in any underwater application. Since the methodology utilizes a normalized quantity, the need for a complete calibration of each individual sensor is eliminated. Hot film sensors are sturdier and less prone to fouling than hot wire sensors. Therefore, this system and the associated sensors require only minimal maintenance. The invention is modular and easy to transport, does not require extensive training or safety procedures for the operator, and is durable with no protruding parts that would be easily broken, making them ideal for underwater applications.

In view of the above detailed description, it is anticipated that the invention herein will have far reaching applications other than those of determining underwater turbulent boundary layer thickness.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed is:

1. A method for determining turbulent boundary layer thickness, comprising the steps of:

mounting a pair of sensors to a solid surface interfacing with a fluid at two separate stream wise locations;

recording a voltage output from said pair of sensors;

computing a real non-dimensional value of a correlation coefficient from said recorded voltage by defining $\xi_n = \hat{\xi}_n \times \delta$ and $T = \hat{T}\delta/U_0$, where $\delta$ is the turbulent boundary thickness and $U_0$ is the ship velocity;

independently determining a laboratory non-dimensional value of the correlation coefficient from laboratory data; and comparing the real non-dimensional value with the laboratory non-dimensional value to obtain a boundary layer thickness having a value which minimizes a difference between the values of the real non-dimensional value and the laboratory non-dimensional value.

2. The method according to claim 1 wherein said hot film sensors are hot film shear stress sensors.

3. A method for determining turbulent boundary layer thickness, comprising the steps of:

mounting a pair of sensors to a solid surface interfacing with a fluid at two separate stream wise locations;

recording a voltage output from said pair of sensors;

computing a real non-dimensional value of a correlation coefficient from said recorded voltage;

independently determining a laboratory non-dimensional value of the correlation coefficient from laboratory data; and comparing the real non-dimensional value with the laboratory non-dimensional value to obtain a boundary layer thickness having a value which minimizes a difference between the values of the real non-dimensional value and the laboratory non-dimensional value;

wherein said correlation coefficient is defined as:

$$R_{\tau_1\tau_2}(\xi_n, T) = \frac{\langle \tau_1(x,t)\tau_2(x+\xi_n, t+T)\rangle}{\sqrt{\langle \tau_1(x,t)^2\rangle}\sqrt{\langle \tau_2(x+\xi_n, t+T)^2\rangle}}$$

where $\tau_1$ and $\tau_2$ are the wall shear stress values at the sensor mounting locations, x is the stream wise coordinate, $\xi_n$ is the discrete sensor spacing, and the < > indicate temporal mean quantities.

4. The method according to claim 3 wherein said step of determining a non-dimensional correlation coefficient is obtained by defining $\xi_n = \hat{\xi}_n \times \delta$ and $T = \hat{T}\delta/U_0$, where $\delta$ is the turbulent boundary thickness and $U_0$ is a vehicle velocity.

5. The method according to claim 4 wherein said non-dimensional correlation coefficient yields a direct relation between the correlation coefficient, $\hat{R}_{\tau_1\tau_2}(\hat{\xi}_n, \hat{T})$ and the turbulent boundary thickness $\delta$.

6. The method according to claim 4 wherein said real non-dimensional correlation coefficient yields a direct relation between the correlation coefficient, $\hat{R}_{\xi_1\tau_2}(\hat{\xi}_n, \hat{T})$ and the turbulent boundary thickness $\delta$.

7. The method according to claim 1 wherein said pair of sensors are housed in a single wall-mountable unit.

8. A turbulent boundary layer thickness sensor for use in a flowing fluid comprising:

a first wall stress shear sensor positionable in contact with said flowing fluid to provide a first wall shear stress measurement;

a second wall stress shear sensor positionable in contact with said flowing fluid relatively downstream from said first wall stress shear sensor to provide a second wall shear stress measurement;

a first analog to digital converter joined to said first wall stress shear sensor to receive said first wall shear stress measurement and to provide a first digital stress measurement;

a second analog to digital converter joined to said second wall stress shear sensor to receive said second wall shear stress measurement and to provide a second digital stress measurement;

a memory element containing tabulated values of the correlation coefficient; and a computer joined to said first and second analog to digital converters to receive the first and second digital stress measurements and to said memory element to estimate said boundary layer value by calculating a real correlation coefficient from the first and second digital stress measurements and comparing the real correlation coefficient with tabulated values of the correlation coefficient from said memory element.

9. The sensor of claim 8 wherein said first and second wall stress shear sensors are hot film sensors.

10. The sensor of claim 9 wherein said first and second wall stress shear sensors are capable of being flush mounted in a wall.

11. The sensor of claim 10 wherein the wall is a hull of a vessel.

12. The sensor of claim 10 wherein the wall is a control surface of a vessel.

* * * * *